United States Patent [19]

Shimizu et al.

[11] Patent Number: 5,496,501
[45] Date of Patent: Mar. 5, 1996

[54] SILACYCLOHEXANE COMPOUND, A METHOD OF PREPARING IT AND A LIQUID CRYSTAL COMPOSITION CONTAINING IT

[75] Inventors: Takaaki Shimizu; Tsutomu Ogihara; Takeshi Kinsho; Tatsushi Kaneko; Ryuichi Saito, all of Niigata; Hideshi Kurihara, Kawasaki, all of Japan

[73] Assignee: Shin-Etsu Chemical Co., Ltd., Tokyo, Japan

[21] Appl. No.: 341,218

[22] Filed: Dec. 5, 1994

[30] Foreign Application Priority Data

Dec. 7, 1993 [JP] Japan .................... 5-339996

[51] Int. Cl.$^6$ .............. C09K 19/34; C07F 7/08
[52] U.S. Cl. .................. 252/299.61; 556/406
[58] Field of Search .......... 252/299.01, 299.61; 556/406; 359/103

[56] References Cited

FOREIGN PATENT DOCUMENTS

| 0355008 | 8/1989 | European Pat. Off. . |
|---|---|---|
| 630903 | 12/1994 | European Pat. Off. . |
| 632044 | 1/1995 | European Pat. Off. . |
| 4014488 | 5/1990 | Germany . |

OTHER PUBLICATIONS

Journal of the American Chemical Society, vol. 94, No. 14, Jul. 12, 1972, pp. 5080–5082, "New Conformationally Stable 4-tert-Butyl-1-silacyclohexanes and Stereochemistry of Insertion of Dimethylsilylenes into the Silicon Hydrogen Bond;"; H. Sakurai, et al.

Liebigs Ann. Chem. No. 9, 1979, pp. 1915–1924; "Derivate des 1-(4-Chlorpheny)silacyclohexans mit 3-(Diethyl-amino)propyl- und 2-(Diethylamino)ethyl-Gruppierungen".

*Primary Examiner*—Shean C. Wu
*Attorney, Agent, or Firm*—Townsend & Banta

[57] ABSTRACT

A silacyclohexane compound represented by the following general formula (I).

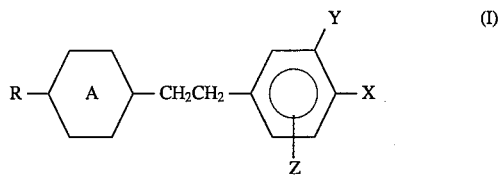

In this formula, R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

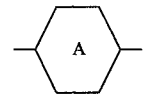

denotes a trans-1-silacyclohexylene or trans-4-silacyclohexylene group whose silicon at position 1 or position 4 has a substitutional group(s) of H, F, Cl or $CH_3$. X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F.

3 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it as well as a liquid crystal display element which contains said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability against moisture, air, light, heat, electric fields, etc., are commonly required in all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are obtained by mixing several to more than ten liquid crystal compounds and latent liquid crystal compounds. Because of this, it is also important that components of a liquid crystal composition mix easily.

The components of the liquid crystal mixture described above can be classified into several categories based on their functions, as shown below:

1) Compounds which contribute to a reduction in viscosity and a lowering of the melting point of the mixed liquid crystal composition
2) Compounds which mainly control the electro-optical functions of the mixed liquid crystal composition
3) Compounds which contribute to raising the clearing point of the mixed liquid crystal composition
4) Compounds which contribute to refraction anisotropy control of the mixed liquid crystal composition
5) Compounds which control the colored display and orientation of the mixed liquid crystal composition For compounds which belong to the category "1) Compounds which contribute to a reduction in viscosity and a lowering of the melting point of the mixed liquid crystal composition" in this classification, compounds with a so-called EPCH structure such as

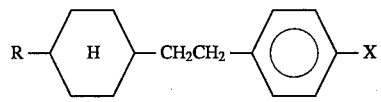

(Japanese examined patent publication (Tokko) Sho 59-35901; X denotes a halogen atom) and

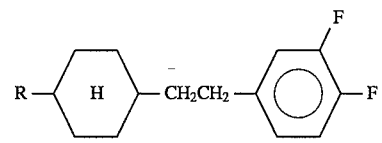

(Tokko Hei 3-46454) have been known.

In recent years, along with the expansion of the applications of liquid crystal displays, the characteristics required of liquid crystal materials are becoming more and more advanced and demanding. In particular, superior characteristics such as a lower driving voltage and improved low temperature performance, compared with conventional liquid crystal substances, are desired.

BRIEF SUMMARY OF THE INVENTION

From such a viewpoint, the object of this invention is to provide a liquid crystal compound containing silacyclohexane rings, which is completely different from the conventional liquid crystal compounds with the EPCH structure as described above.

That is, this invention is a silacyclohexane compound represented by the following general formula (I).

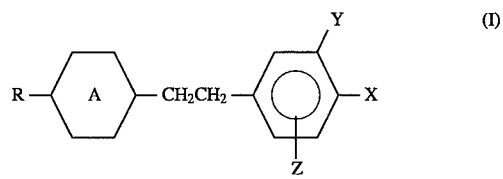

In this formula, R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

The group

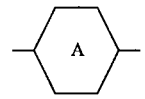

denotes trans-1-silacyclohexylene or trans-4-silacyclohexylene group whose silicon at position 1 or position 4 has a substitutional group(s) of H, F, Cl or $CH_3$.

X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F.

This invention is also a method of preparing the silacyclohexane compound represented by the general formula (I), characterized by the use of a carbon-carbon bond formation reaction or a carbon-silicon bond formation reaction between an organometallic reagent

R—M and

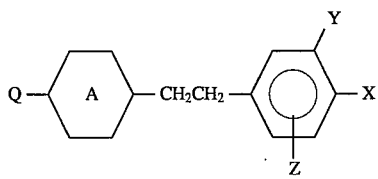

(M denotes MgP (P denotes a halogen atom), ZnP or Li, and Q denotes a halogen atom, or an alkoxy, methanesulfonyl, benzenesulfonyl or p-toluenesulfonyl group).

Furthermore, this invention is a method of preparing the silacyclohexane compound represented by the general formula (I), characterized by the use of a carbon-carbon bond formation reaction or a carbon-silicon bond formation reaction between an organometallic reagent

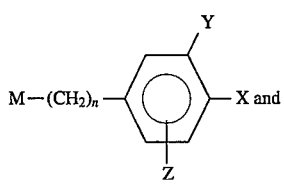

(M denotes MgP, ZnP (P denotes a halogen atom) or Li; Q denotes a halogen atom, or an alkoxy, methanesulfonyl, benzenesulfonyl or p-toluenesulfonyl group; and n and m are the integers 0, 1 or 2 with n+m=2).

Furthermore, this invention is a method of preparing the silacyclohexane compound represented by the general formula (I), characterized by the use of a carbon-carbon bond formation reaction between an organometallic reagent

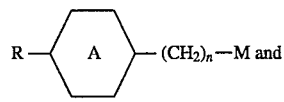

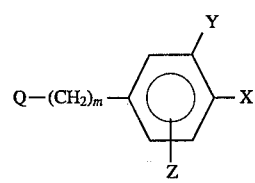

(M denotes MgP (P denotes a halogen atom), ZnP or Li, and Q denotes a halogen atom, or an alkoxy, methanesulfonyl, benzenesulfonyl or p-toluenesulfonyl group).

Furthermore, this invention is a liquid crystal composition characterized by containing the silacyclohexane compound represented by the general formula (I), and a liquid crystal display element which uses this composition.

DETAILED DESCRIPTION

This invention is described in detail below. The new compounds represented by said general formula (I) are silacyclohexane compounds whose ring structure has one trans-1 or 4-silacyclohexane ring, specifically represented by the general formulas (II) or (III) shown below:

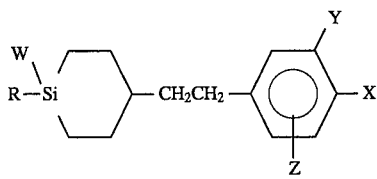

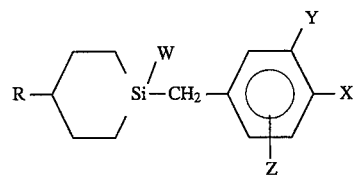

R denotes the following groups listed in (a) through (e):
  (a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group
  (b) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl or 10,10-difluorodecyl group
  (c) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group
  (d) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxyopropyl, ethoxypropyl, propoxypropyl, butoxypropyl, methoxybutyl, ethoxybutyl, methoxypentyl or ethoxypentyl group (e) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group W denotes H, F, Cl or $CH_3$. X denotes a CN, F, Cl, $CF_3$, $CF_2Cl$, CHFCl, $OCF_3$, $OCF_2Cl$, OCHFCl, $OCHF_2$, R or OR group. Y denotes H or F. Z denotes H or F. The group

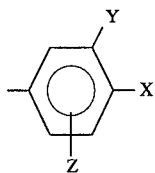

specifically denotes groups shown below:

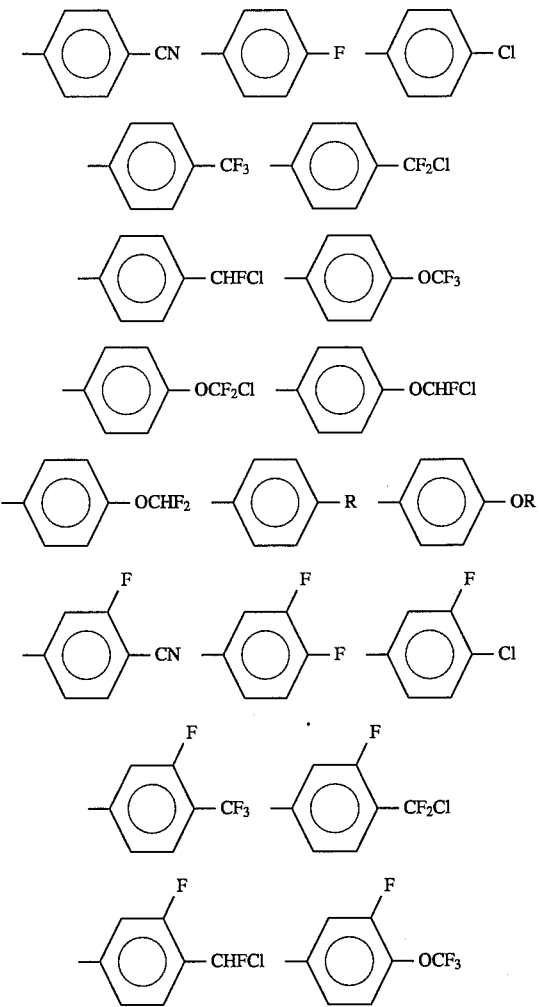

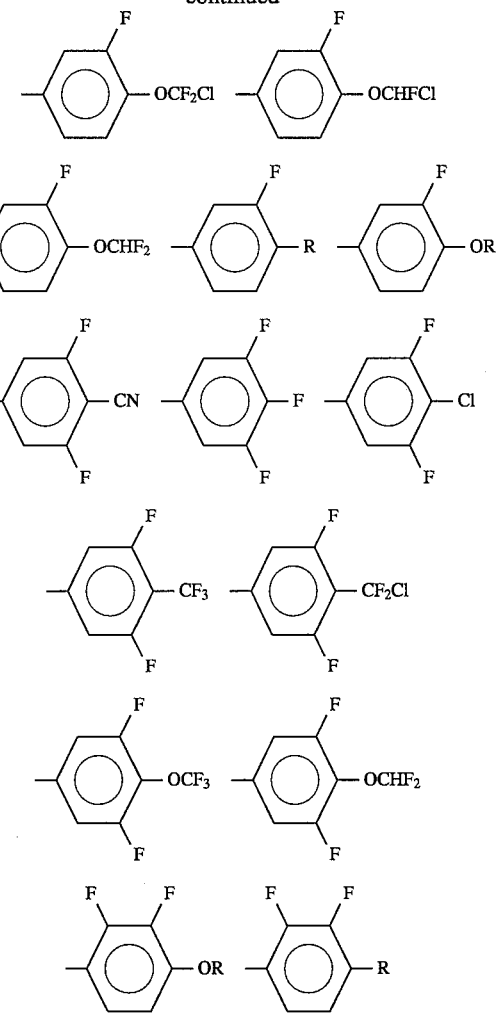

For the ring structure, compounds represented by the general formula (II) are desirable for practical use.

For R, the following groups listed in (a) through (e) are desirable for practical use:

(a) A linear-chain alkyl group with a carbon number of 2–7, i.e. an ethyl, n-propyl, n-butyl, n-pentyl, n-hexyl or n-heptyl group (b) Some mono- or di-fluoroalkyl groups with a carbon number of 1–10 including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups (c) Some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (d) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (e) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and CH, groups are desirable for W in practical use. Groups desirable in practical use for the group

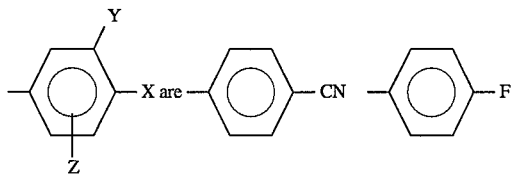

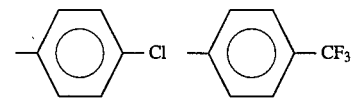

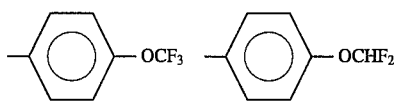

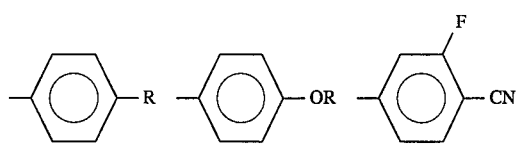

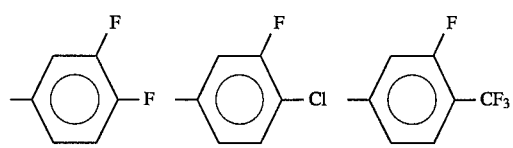

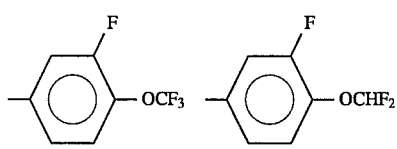

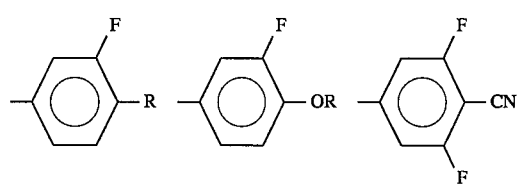

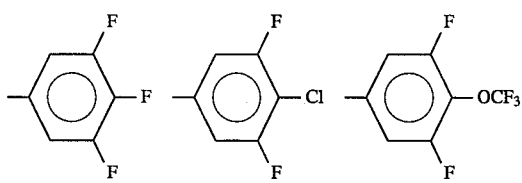

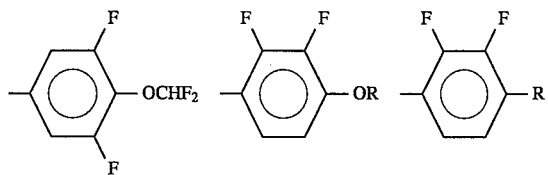

The manufacturing methods of these compounds are described next. These compounds are prepared by carbon-carbon bond formation reaction or carbon-silicon bond formation reaction between an organometallic reagent and a compound which has an eliminatable group(s) such as a halogen atom, alkoxy, methanesulfonyl, benzenesulfonyl or p-toluenesulfonyl group. A detailed description is given below.

In the reaction between the organometallic reagent
R—M
and the compound

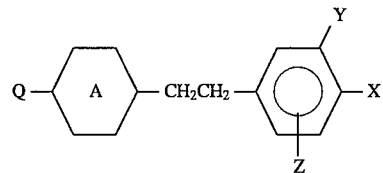

(M denotes MgP (P denotes a halogen atom), ZnP or Li, and Q denotes a halogen atom, or an alkoxy, methanesulfonyl, benzenesulfonyl or p-toluenesulfonyl group), when the group

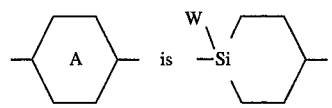

(W denotes H, F, Cl or CH$_3$), Q is a halogen atom or an alkoxy group, for example. Particularly, if Q is a Cl or Br atom, or an OCH$_3$ or OCH$_2$CH$_3$ group, then the carbon-silicon bond formation reaction proceeds easily and gives a high yield of the target product.

When the group

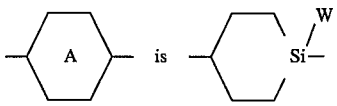

this carbon-carbon bond formation reaction is carried out in the presence of a catalytic amount of copper salt. In this case, Q is a halogen atom or a sulfonyl group, for example. It is particularly preferable if Q is Br, I or a p-toluenesulfonyl group because then the target product can be obtained with a high yield.

In the reaction between the organometallic reagent

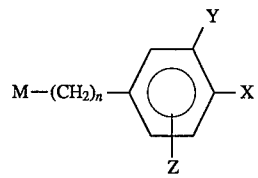

and the compound

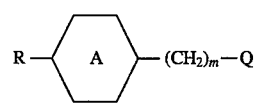

if n=2 and the group

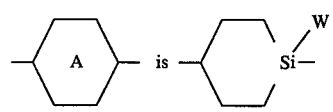

then Q is a halogen atom or an alkoxy group, for example. Particularly, if Q is a Cl or Br atom, or an OCH$_3$ or OCH$_2$CH$_3$ group, then the carbon-silicon bond formation reaction proceeds easily and gives a high yield of the target product.

If n=2 and the group

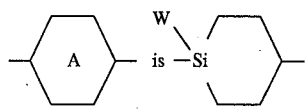

then Q is a halogen atom or a sulfonyl group, for example. Particularly, if Q is Br, I, or a p-toluenesufonyl group, then the carbon-carbon bond formation reaction proceeds easily and gives a high yield of the target product.

When n is not 2, i.e. in the case of the reaction between the organometallic reagent

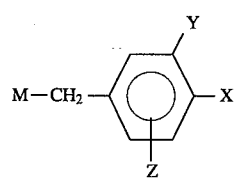

and the compound

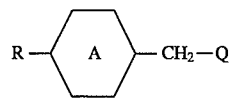

or in the case of the reaction between the organometallic reagent

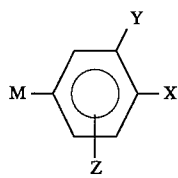

and the compound

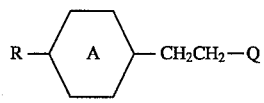

Q is a halogen atom or a sulfonyl group, for example. Particularly, if Q is Br, I, or a p-toluenesufonyl group, then the carbon— carbon bond formation reaction proceeds easily and gives a high yield of the target product.

On the other hand, in the reaction between the organometallic reagent

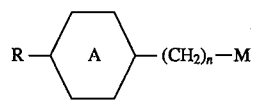

and the compound

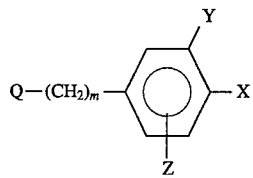

if n is not 2, i.e. in the case of the reaction between the organometallic reagent

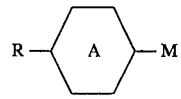

and the compound

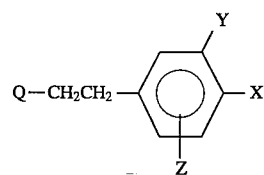

or in the case of the reaction between the organometallic reagent

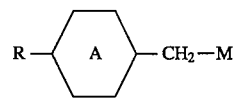

and the compound

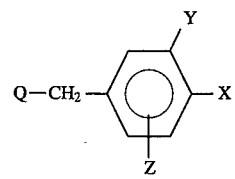

these carbon-carbon bond formation reactions are carried out in the presence of a catalytic amount of copper salt.

Q is a halogen atom or a sulfonyl group, for example. It is particularly preferable if Q is Br, I or a p-toluenesulfonyl group because then the target product can be obtained with a high yield.

If n=2, i.e. the reaction between the organometallic reagent

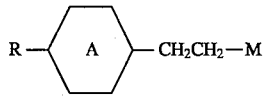

and the compound

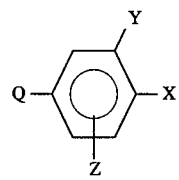

is carried out in the presence of a transition metal catalyst. Palladium compounds and nickel compounds are particularly preferable for the catalyst.

Q denotes a halogen atom. Cl, Br and I all give a high yield of the target product if an appropriate catalyst is chosen.

The compound produced here may be a mixture of trans isomers and cis isomers in terms of the conformation of the silacyclohexane ring. If this is the case, then a conventional purification means such as chromatography and recrystallization is employed to separate the trans isomers to obtain the silacyclohexane compound of this invention represented by the general formula (I).

The silacyclohexane compound of this invention can be mixed with known compounds to obtain a liquid crystal composition. The compound used for mixing to obtain the liquid crystal compound can be chosen from among the known compounds shown below:

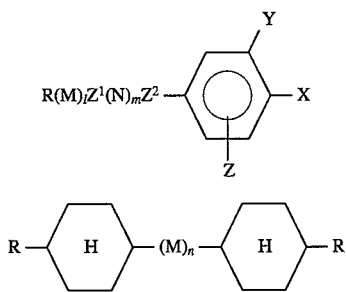

In the above formulas, (M) and (N) denote one of the following:

1) A trans-1,4-cyclohexylene group which has no substitution or which has one or more substitutional groups such as F, Cl, Br, CN or alkyl groups
2) A trans-1,4-cyclohexylene group in which O or S is substituted for one or nonadjacent two $CH_2$ groups in the cyclohexane ring
3) A 1,4-cyclohexenylene group
4) A 1,4-phenylene group which has no substitution or which has one or two substitutional groups such as F, Cl, $CH_3$ or CN groups
5) A 1,4-phenylene group in which an N atom is substituted for one or two CH groups in the ring $Z^1$ and $Z^2$ denote —$CH_2CH_2$—, —CH=CH—, —C≡C—, —$CO_2$—, —OCO—, —$CH_2O$—, —$OCH_2$— or a single bond.

l, m=0, 1 or 2 (where l+m=1, 2 or 3), and n=0, 1 or 2.

R denotes hydrogen, a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F.

In the above description, if l=2 and n=2, then (M) can contain heterogeneous rings, and if m=2, then (N) can contain heterogeneous rings.

The ratio of one or more types of the silacyclohexane compound of this invention contained in the liquid crystal composition is 1–50 wt %, more preferably 5–30 wt %. The liquid crystal composition can also contain a polygenetic dye(s) to generate the colored guest-host system and additives to change the dielectric anisotropy, viscosity and the orientation of the nematic phase.

The liquid crystal composition thus formed is sealed between transparent plates which have electrodes of desired shapes and thus used as liquid crystal display elements. This element can have various undercoatings, overcoatings for the orientation control, a polarizer plate(s), a filter(s) and a reflector layer(s), as necessary. It can be made into a laminated cell or combined with other display elements. Semiconductor substrates and light sources can also be used to make various types of displays.

For the mode of the liquid crystal display element, prior-art methods in the industry of liquid crystal display elements, such as the dynamic scattering (DSM) method, the twisted nematic (TN) method, the super twisted nematic (STN) method, the guest-host (GH) method and the polymer dispersion liquid crystal (PDLC) method can be adopted.

EXAMPLES

The details of this invention are described below by referring to specific examples.

EXAMPLE 1

Preparation of trans-4-(2-(3,4-difluorophenyl)ethyl)-1-n-pentyl-1-silacyclohexane 60 ml of a THF solution of 2.0M n-pentylmagnesium chloride was dripped into a mixture of 27.5 g (100 mmol) of 1-chloro-4-(2-(3,4-difluorophenyl)ethyl)-1-silacyclohexane and 200 ml of tetrahydrofuran (hereafter referred to as "THF"). The silacyclohexane rings of the target product thus obtained were a mixture of trans isomers and cis isomers. After a conventional after treatment, they were separated by means of chromatography to obtain 21.1 g of the trans isomers (yield 68%), which was the target product. This compound was in a liquid form at temperatures down to −60° C.

The following compounds were obtained in the same manner as Example 1.

EXAMPLE 2

Trans-4-(2-(p-fluorophenyl)ethyl)-1-n-pentyl-1-silacyclohexane

IR vmax: 2918, 2852, 2098, 1601, 1510, 1223, 887 and 823 $cm^{-1}$ C-I transition temperature: −23.7° C., N-I transition temperature: −54° C.

EXAMPLE 3

Trans-1-n-pentyl-4-(2-(p-trifluoromethoxyphenyl)ethyl)-1-silacyclohexane

EXAMPLE 4

Preparation of trans-4-(2-(3,4-difluorophenyl)ethyl)-1-isopentyl-1-silacyclohexane 65 ml of a Grignard's reagent (1.0M THF solution) prepared from 4-bromomethyl-1-isopentyl-1-silacyclohexane was dripped into a mixture of 10.4 g (50.2 mmol) of 3,4-difluorobenzylbromide, 200 mg of copper iodide (I), 400 mg of triethylphosphite and 100 ml of THF. After a conventional after treatment, they were separated by means of chromatography to obtain 11.7 g of the target product (yield 75%).

The following compounds were obtained in the same manner as Example 4.

EXAMPLE 5 trans-4-(2-(4-chloro-3-fluorophenyl)ethyl)-1-(5-methoxypentyl)-1-silacyclohexane

EXAMPLE 6 trans-4-(2-(p-ethoxyphenyl)ethyl)-1-(1-pentenyl)-1-silacyclohexane

EXAMPLE 7

Preparation of trans-4-(2-(p-cyanophenyl)ethyl)-1-n-pentyl-1-silacyclohexane 250 ml of an organozinc compound (1.0M THF solution) prepared from trans-4-(2-bromoethyl)-1-n-pentyl-1-silacyclohexane was dripped into a mixture of 45.5 g (0.25 mmol) of p-bromobenzonitrile, 500 mg of tetrakis (triphenylphosphine) palladium (0) and 500 ml of THF. After a conventional after treatment, they were separated by means of chromatography to obtain 49.4 g of the target product (yield 66%).

The following compounds were obtained in the same manner as Example 7.

EXAMPLE 8 trans-1-(2-(4-cyano-3-fluorophenyl)ethyl)-4-n-heptyl-1-methyl-1-silacyclohexane

EXAMPLE 9

Preparation of trans-4-(2-ethoxyphenyl)ethyl)-1-n-pentyl-1-silacyclohexane

A catalytic amount of a THF solution of dilithiumtetrachloro cuprate was dripped into a mixture of 22.9 g (100 mmol) of p-(2-bromoethyl) ethoxybenzene and 100 ml of THF, and then 90 ml of a Grignard's reagent (1.0M THF solution) prepared from 4-bromo-1-n-pentyl-1-silacyclohexane was dripped into this. The silacyclohexane rings of the target product thus obtained were a mixture of trans isomers and cis isomers. After a conventional after treatment, they were separated by means of chromatography to obtain 25.2 g of the target product (yield 88%).

IR vmax: 2918, 2852, 2098, 1612, 1512, 1244, 1051, 887 and 822 cm$^{-1}$ C-I transition temperature: 0.2° C. N-I transition temperature: −1.7° C.

The following compounds were obtained in the same manner as Example 9.

EXAMPLE 10 trans-4-(2-(p-difluoromethoxyphenyl)ethyl)-1-fluoro-1-n-pentyl-1-silacyclohexane

EXAMPLE 11 trans-1-n-pentyl-4-(2-(p-trifluoromethylphenyl)ethyl)-1-silacyclohexane

EXAMPLE 12 trans-1-n-pentyl-4-(2-(2,3-difluoro-4-ethoxyphenyl)ethyl)-1-silacyclohexane

IR (liquid film) vmax: 2956, 2920, 2852, 2098, 1639, 1512, 1479, 1292, 1080, 887, 831 and 816 cm$^{-1}$ C-I transition temperature: 12.4° C. N-I transition temperature: −17.8° C.

EXAMPLE 13 trans-1-(4-fluoropentyl)-4-(2-(p-fluorophenyl)ethyl)-1-silacyclohexane

EXAMPLE 14 trans-1-n-pentyl-4-(2-(p-(3-fluorobutyl)phenyl)ethyl)-1-silacyclohexane

EXAMPLE 15 trans-1-(3-methoxypropyl)-4-(2-(p-fluorophenyl)ethyl)-1-silacyclohexane

EXAMPLE 16 trans-1-(3-methylbutyl)-4-(2-(p-fluorophenyl)ethyl)-1-silacyclohexane

EXAMPLE 17 trans-1-(4-pentenyl)-4-(2-(p-fluorophenyl)ethyl)-1-silacyclohexane

Example of a liquid crystal composition

A liquid crystal composition comprising a mixture, with a weight ratio 2:1:1, of trans-4-(2-(trans-4-(3,4-difluorophenyl)cyclohexyl)ethyl)-1-n-ethylcyclohexane, trans-4-(2-(trans-4-(3,4-difluorophenyl)cyclohexyl)ethyl)-1-n-propylcyclohexane and trans-4-(2-(trans-4-(3,4-difluorophenyl)cyclohexyl)ethyl)-1-n-pentylcyclohexane was sealed in a TN cell. This had a threshold voltage of 2.46 V and a viscosity at 5° C. of 96 cp.

A mixture prepared by adding 20 wt % of the trans-4-(2-(3,4-difluorophenyl)ethyl)-1-n-pentyl-1-silacyclohexane obtained in Example 1 to this mother liquid crystal had a threshold voltage of 2.05 V and a viscosity at 5° C. of 50 cp.

When the liquid crystal compounds of this invention which have Si as a ring composing element are used as components of the liquid crystal phase, there are the following advantages over liquid crystal compounds which have a conventional EPCH structure comprising similar hydrocarbon rings.

Since they have the nematic liquid crystal phase extended to low temperatures, their low temperature performance improves, i.e. the viscosity at low temperatures decreases, the response time at low temperatures improves, mutual solubility at low temperatures improves, and so on.

Also, liquid crystal compounds represented by the general formula (1), except for those whose substitutional groups Y and Z are H and X is R or OR, have, in addition to the advantages mentioned above, an effect of lowering the threshold voltage because of a greater dielectric anisotropy.

The liquid crystal compound whose substitutional groups Y and Z are H and X is R or OR in the general formula (1) has near-zero dielectric anisotropy, and therefore it should preferably be used for the liquid crystal phase for display based on dynamic scattering (DS) or deformation of aligned phase (DAP mode). The compounds other than these should preferably be used for manufacturing the liquid crystal phase with a large positive dielectric anisotropy which is used in display elements based on the twisted nematic cell or the cholesteric-nematic phase transition.

Of the silacyclohexane compounds of this invention, those which show a monotropic phase transition or a crystal-isotropic liquid type transition do not show the electro-optical characteristics of liquid crystals when used alone. they contribute to a reduction in the viscosity and a lowering of the melting point when used with other components in a mixture.

We claim:

1. A silacyclohexane compound represented by the following general formula (I):

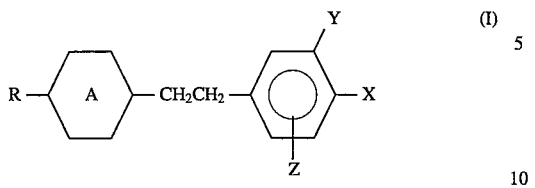

In this formula, R denotes a linear-chain alkyl group with a carbon number of 1–10, a mono- or di-fluoroalkyl group with a carbon number of 1–10, a branched-chain alkyl group with a carbon number of 3–8, an alkoxy-alkyl group with a carbon number of 2–7, or an alkenyl group with a carbon number of 2–8;

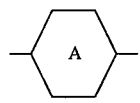

denotes a trans-1-silacyclohexylene or a trans-4-silacyclohexylene group whose silicon at position 1 or position 4 has a substitutional group(s) of H, F, Cl or $CH_3$; X denotes a CN, F, Cl, $CF_3$, $CF_2Cl$, CHFCl, $OCF_3$, $OCHF_2$, $OCF_2Cl$, OCHFCl, R or OR group; Y denotes H or F; Z denotes H or F.

2. A liquid crystal composition characterized by containing the silacyclohexane compound as described in claim 1.

3. A liquid crystal display element characterized by containing the liquid crystal composition as described in claim 2.

* * * * *